(12) United States Patent
Gillings et al.

(10) Patent No.: US 6,238,352 B1
(45) Date of Patent: May 29, 2001

(54) INHALATION TESTING METHOD AND MEANS

(75) Inventors: Robert Gillings, Bishops Stortford; David William Spencer, Enfield, both of (GB)

(73) Assignee: Clement Clarke International, Ltd., Harlow (GB)

( * ) Notice: Subject to any disclaimer, the term of this patent is extended or adjusted under 35 U.S.C. 154(b) by 0 days.

(21) Appl. No.: 09/255,863

(22) Filed: Feb. 23, 1999

(30) Foreign Application Priority Data

Feb. 24, 1998 (GB) .................................................. 98039022

(51) Int. Cl.[7] .................................................... A61B 05/08
(52) U.S. Cl. ............................................. 600/538; 600/529
(58) Field of Search ..................................... 600/538, 529, 600/532, 533; 482/13; 128/200.23, 200.11, 200.12, 200.24, 203.23, 204.24, 204.25

(56) References Cited

U.S. PATENT DOCUMENTS

| | | |
|---|---|---|
| 3,695,608 | 10/1972 | Hanson . |
| 4,114,607 | 9/1978 | Russo . |
| 4,158,360 | 6/1979 | Adams . |
| 4,693,256 | 9/1987 | Talonn . |
| 5,287,851 | * 2/1994 | Beran et al. .................... 600/538 |
| 5,522,380 | 6/1996 | Dwork . |
| 5,564,432 | 10/1996 | Thomson . |

* cited by examiner

*Primary Examiner*—Robert L. Nasser
(74) *Attorney, Agent, or Firm*—Jones, Tullar & Cooper PC

(57) ABSTRACT

An inhalatory flow meter with a restriction flow meter with a restriction device located in the air flow path through the meter for increasing the resistance to flow through the meter. The restriction device may be removable or adjustable or capable of being rendered inoperative. A plurality of alternative restriction devices may be used interchangeably with the inhalatory flow meter, each having a predetermined pressure:flow rate characteristic.

Also provided is a method of testing the performance of a subject in relation to the use of an inhalatory dispensing device for the introduction of a substance to the airways of the subject. In the method an inspiratory flow meter is provided with a predetermined flow restriction to provide a comparison with the resistance of the inhalatory dispensing device in use.

20 Claims, 2 Drawing Sheets

INHALATION TESTING METHOD AND MEANS

BACKGROUND OF THE INVENTION

This invention relates to a method and means which allow the flow characteristics of inhalatory devices to be simulated, for example for the evaluation of the suitability of those devices for particular subjects.

In the treatment of various physiological conditions of the airways it is known to provide dispensing devices to deliver doses of particular substances by inhalation for therapy or control of those conditions. For a number of reasons, such as the fact that many of the conditions for which these substances are intended are caused by impaired lung or bronchial function, the efficiency of delivery of the materials can vary significantly from subject to subject.

SUMMARY OF THE INVENTION

In one of its aspects, the present invention provides a method of testing the performance of a subject in relation to the use of an inhalatory dispensing device for the introduction of a substance to the airways of the subject, in which an inspiratory flow meter is provided with a predetermined flow restriction to provide a comparison with the resistance of the inhalatory dispensing device in use.

According to another aspect of the invention, an inhalatory flow meter is provided in combination with a restriction device located in the air flow path through the meter for increasing the resistance to flow through the meter, said device being removable or adjustable or being capable of being rendered inoperative.

For many purposes it will be convenient to have a plurality of alternative restriction devices to be used interchangeably with the inhalatory flow meter, each having a predetermined pressure: flow rate characteristic, which may be illustrated for example in the form of a calibration chart. It may be preferred to provide a series of disposable restriction devices for use in accordance with the invention.

It is known to provide an inhalatory flow meter with a removable or disposable adaptor which comprises or carries a mouthpiece through which the subject inhales. In a convenient form of the invention, such an adaptor or mouthpiece can incorporate a restriction device, eg. in the form of an orifice.

The invention will be described further by way of example with reference to the accompanying drawings.

DESCRIPTION OF THE PREFERRED EMBODIMENTS

Figure 1:
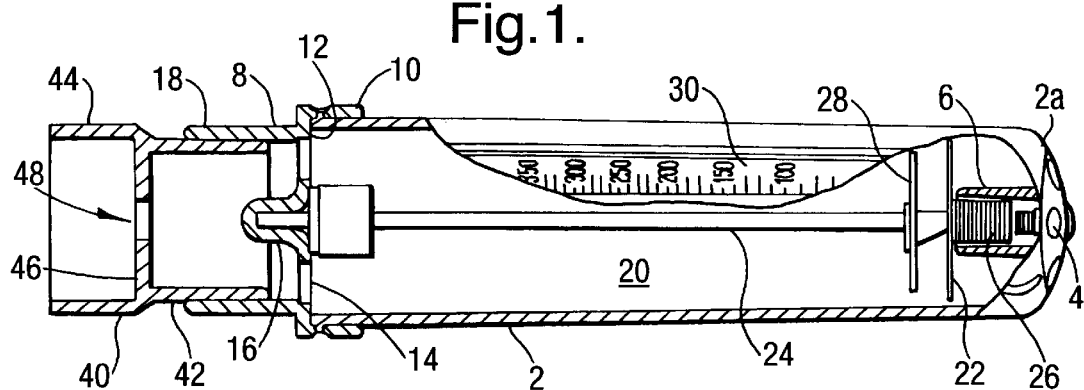
FIG. 1 illustrates an inhalation meter provided with a restriction device according to the invention.

In FIG. 1 an inhalatory flow meter tool is shown which, in known manner, has an elongate hollow body 2 of transparent plastics closed at one end by an integral wall 2a having a ring of apertures 4 surrounding a first central boss 6, and at the other end by an end member 8 secured to the casing by a cylindrical flange 10 and similarly comprising a wall 12 having a ring of apertures 14 surrounding a second central boss 16. A concentric spigot 18 projecting from the end member 8 can receive releasably an adaptor or an extension mouthpiece, as will be described below.

The internal chamber 20 formed between the end walls 2a,12 is divided by a piston 22 which is slidable on a guide rod 24 mounted in the bosses 6,16. A coil spring 26 connected between the piston 22 and the first boss 6 draws the piston to one end of the body 2, as shown. An indicator 28 on the opposite side of the piston 22 to the spring 26 is also mounted on the guide rod 24 and engages the rod with a light frictional force. A scale 30 is marked along the casing wall to show the position of the indicator.

Figure 2:
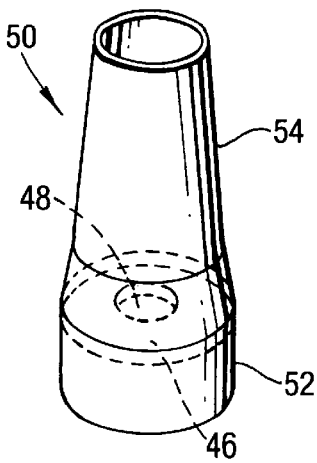
FIG. 2 illustrates an alternative restriction device for use with the meter of FIG. 1.
Figure 3:
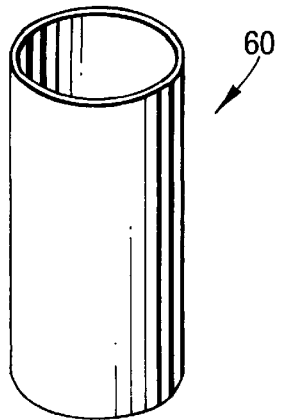
FIG. 3 illustrates a mouthpiece for use with the meter of FIG. 1, FIGS. 4a and 4b illustrate an alternative mouthpiece and adaptor.

FIG. 1 shows the meter provided with an intermediate adaptor 40 incorporating a restriction device in accordance with the invention, but conventionally an unrestricted mouthpiece extension, such as those shown in FIGS. 2 to 4, is releasably gripped in the cylindrical spigot 18 of the end member 8. When a subject inhales through the mouthpiece extension, air is drawn through the chamber 20 by way of the apertures 4,14 to displace the piston 22 against the force of the spring 26. The indicator 28 is entrained by the piston and its frictional engagement with the guide rod 24 leaves it in a displaced position after the inhalation has ceased and the piston has been withdrawn by the spring. The position reached can be recorded from the scale 30 before the indicator is returned to the end of the chamber for a further operation.

The conventional meter is constructed so that substantially the only resistance to flow is provided by the piston and the spring force is chosen in order to allow the piston to move relatively freely over the extent of the scale measuring peak inspiratory flow. In the present case, however, the resistance to flow is increased in order to simulate the resistance that would be experienced when using an inhalatory treatment delivery device.

FIG. 1 shows the restriction device provided as an integral part of the intermediate adaptor 40 frictionally engaged by a smaller cylindrical flange 42 in the spigot 18 and having a larger cylindrical spigot 44 a mouthpiece extension thus being engageable in the spigot 44 as in the spigot 18. Between the flange 42 and the spigot 44, the adaptor has an integral diaphragm plate 46 provided with an orifice 48 which creates an increased resistance to flow through the meter.

FIG. 2 illustrates a mouthpiece extension 50 largely of conventional form, comprising a cylindrical flange 52 for frictional engagement with the end member spigot 18 and a tapering mouthpiece portion 54. FIG. 2 also shows, within the mouthpiece extension, an integral diaphragm plate 46 and orifice 48 corresponding to the plate and orifice of the intermediate adaptor in FIG. 1 and thus indicated by the same reference numbers.

It will be understood that, alternatively, a conventional mouthpiece extension without a restricting diaphragm plate and orifice, but otherwise as illustrated in FIG. 2, can be employed with the intermediate adaptor 40 of FIG. 1. Similarly, the mouthpiece extension 60 of FIG. 3 intended for adults, or the pediatric mouthpiece extension 62 of FIG. 4a, can be employed with the intermediate adaptor 40 in the same manner, the latter being connected to the spigot 44 by means of the additional adaptor piece 64 shown in FIG. 4b. As is known, these mouthpieces are typically intended to be disposable.

Figure 4A:
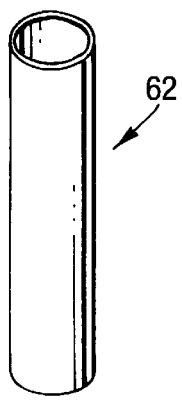
Figure 4B:
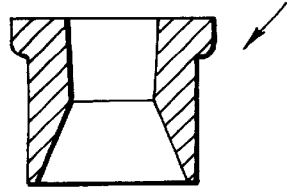

It will also be understood that the intermediate adaptor can be dispensed with, if, like the mouthpiece extension of FIG. 2, the mouthpiece extensions 60,62 of FIG. 3 or FIG. 4a, or the adaptor piece 64 of FIG. 4b, were to be provided with a restriction device.

Figure 5:
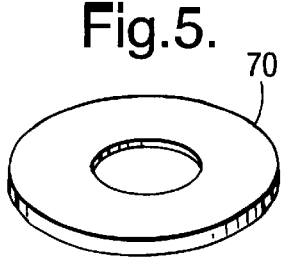
FIG. 5 illustrates a further restriction device.

The restriction device can be formed as a separate element, such as the orifice plate 70 shown in FIG. 5, for insertion into an adaptor or a mouthpiece extension. If alternative restriction effects are to be reproduced, the same adaptor or mouthpiece extension can thus be easily modified to give the required effect by substituting different orifice plates. It is also possible to provide a series of adaptors such as the adaptor 40, or mouthpiece extensions such as that in FIG. 2, with integral restrictions of different characteristics for the same purpose.

Figure 7:
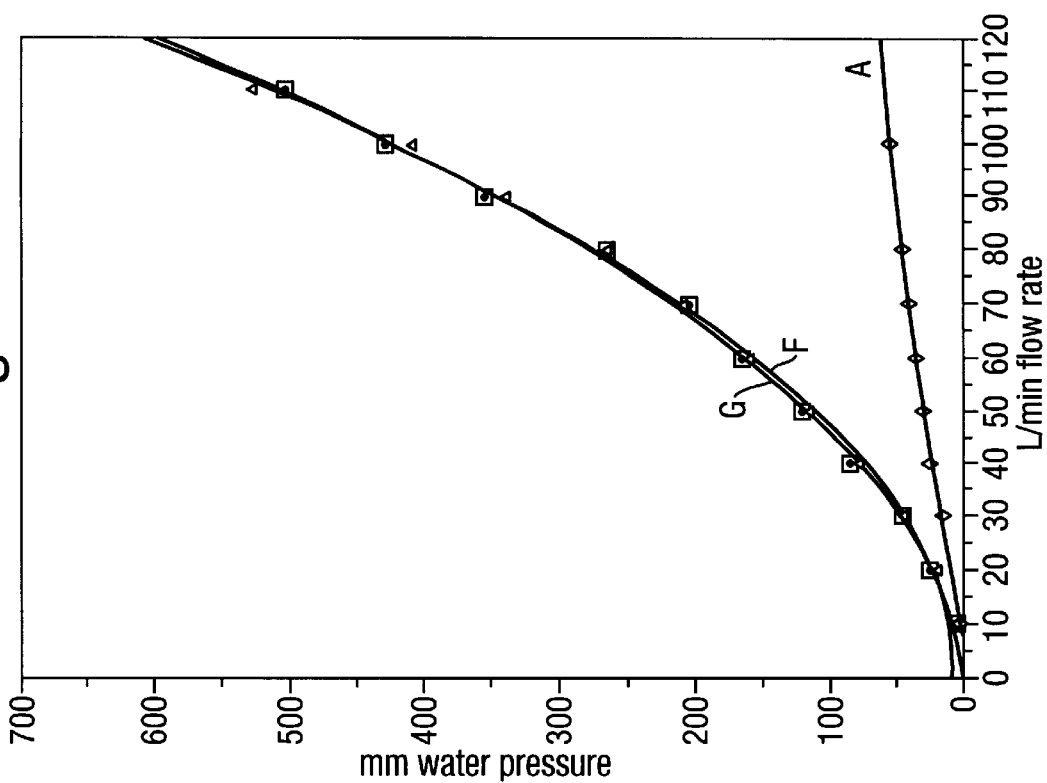
FIG. 7 is a further graph comparing the flow characteristics of one inhalatory dispensing device with those of a meter provided with the appropriate restriction device according to the invention.
Figure 6:
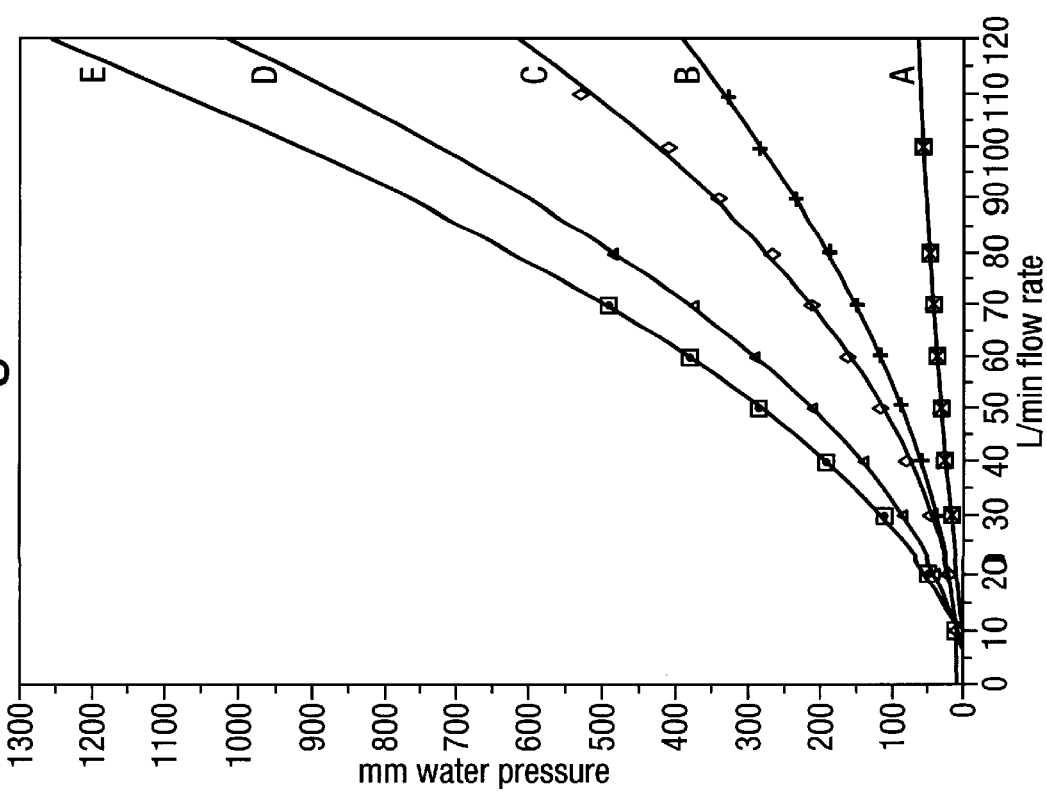
FIG. 6 is a graph illustrating a series of pressure: air flow characteristics for the imitation of specific inhalation material delivery devices.

As already indicated, in the use of the invention, the effect of the restriction device is to increase the resistance to flow through the meter when the subject inhales. FIG. 6 shows in the characteristic curve A, the pressure: air flow characteristic of the meter 2 when the restriction device 12 is absent. Alternative adaptors 40 with different restriction devices give different characteristic curves B, C, D or E. The restrictions in these alternative mouthpieces have been designed to mimic the air resistance offered by specific proprietary delivery devices, such as the Glaxo-Wellcome Accuhaler or the Astra Turbohaler, by the use of which subjects can inhale treatment substances into their airways. This is exemplified in FIG. 7, where the characteristic pressure: flow rate curve A again shows the meter used with a normal mouthpiece, curve F show the characteristic of a particular inhalatory delivery device, and curve G the characteristic of the meter when the appropriate restriction device is used.

Many modifications can be made within the scope of the invention.

For example, although the restriction devices described above are provided at the exit from the meter, they can also be arranged on the entry side of the meter.

Also, although the restriction devices have been described above as a series of alternative devices each of fixed resistance, it is possible within the scope of the invention to provide an adjustable restriction device, or a number of devices that can be used in different combinations to provide the required alternative characteristics.

Furthermore, the restriction, shown as a simple orifice, can take a variety of forms, for example being provided by an open pore structure or a multiplicity of small channels.

What is claimed is:

1. In combination:
   (a) an inhalatory flow meter comprising a body provided with an air inlet and a mouthpiece outlet, an air flow path extending between said inlet and outlet, and an indicator operable in response to inhalatory flow along said air flow path, whereby said meter is capable of providing a measure of inspiratory flow; and
   (b) a restriction device located in said air flow path for increasing resistance to air flow along said air flow path of the meter, the restriction device having a predetermined pressure:flow characteristic, wherein there is provided a plurality of said restriction devices, each said restriction device having a predetermined pressure:flow rate characteristic.

2. The combined inhalatory flow meter and restriction device of claim 1 wherein the restriction device is removable.

3. The combined inhalatory flow meter and restriction device of claim 2 wherein the body of said inhalatory flow meter comprises a main casing and a mouthpiece removable from the casing, wherein the restriction device is contained in the removable mouthpiece.

4. The combined inhalatory flow meter and restriction device of claim 3 wherein the restriction device is replaceably locatable in the mouthpiece.

5. The combined inhalatory flow meter and restriction device of claim 3 wherein the mouthpiece is disposable.

6. The combined inhalatory flow meter and restriction device of claim 1 wherein the body of said inhalatory flow meter comprises a main casing, a mouthpiece, and an adaptor replaceably locatable between the mouthpiece and the main casing of the meter to connect the mouthpiece to the main casing, wherein the restriction device is contained in the adaptor.

7. The combined inhalatory flow meter and restriction device of claim 6 wherein the restriction device is replaceably locatable in the adaptor.

8. The combined inhalatory flow meter and restriction device of claim 1 wherein the restriction device comprises an orifice plate.

9. The combined inhalatory flow meter and restriction device of claim 1 wherein the restriction device is adjustable.

10. The combined inhalatory flow meter and restriction device of claim 1 wherein the restriction device can be rendered inoperative.

11. The combined inhalatory flow meter and restriction device of claim 1, wherein each of the plurality of restriction devices is arranged to give the meter a different, predetermined pressure:flow rate characteristic.

12. A kit for use in the simulation of inhalatory flow meters of different characteristics, the kit comprising:
   (a) an inhalatory flow meter comprising a body provided with an air inlet and a mouthpiece outlet, an air flow path extending between said inlet and outlet, and an indicator operable in response to inhalatory flow along said air flow path, whereby said meter is capable of providing a measure of inspiratory flow; and
   (b) a plurality of a restriction devices to be alternatively located in said air flow path for increasing resistance to air flow along said air flow path of the meter, the restriction devices having predetermined pressure:flow characteristic.

13. The kit of claim 12 wherein the body of said inhalatory flow meter comprises a main casing and a mouthpiece removable from the casing, and wherein the restriction devices are replaceably locatable in the removable mouthpiece.

14. The kit of claim 13 wherein the mouthpiece is disposable.

15. The kit of claim 12 wherein the body of said inhalatory flow meter comprises a main casing, a mouthpiece, and an adaptor replaceably locatable between the mouthpiece and the main casing of the meter to connect the mouthpiece to the main casing, wherein the restriction devices are contained in the adaptor.

16. The kit of claim 15 wherein the restriction devices are replaceably locatable in the adaptor.

17. The kit of claim 12 wherein each said restriction device comprises an orifice plate.

18. The kit of claim 12 wherein each of the plurality of restriction devices is arranged to give the meter a different, predetermined pressure:flow rate characteristic.

19. In combination:

(a) an inhalatory flow meter comprising a body provided with an air inlet and a mouthpiece outlet, an air flow path extending between said inlet and outlet, and an indicator operable in response to inhalatory flow along said air flow path, whereby said meter is capable of providing a measure of inspiratory flow; and (b) a removable restriction device located in said air flow path for increasing resistance to air flow along said air flow path of the meter, the restriction device having a predetermined pressure:flow characteristic, wherein there is provided a series of said restriction devices, each said restriction device having a different predetermined pressure:flow rate characteristic.

20. The combined inhalatory flow meter and restriction device of claim 19 wherein the restriction device comprises an orifice plate.

* * * * *

UNITED STATES PATENT AND TRADEMARK OFFICE
CERTIFICATE OF CORRECTION

PATENT NO. : 6,238,352 B1
DATED : May 29, 2001
INVENTOR(S) : Robert Gillings: David William Spencer It is certified that error appears in the above-identified patent and that said Letters Patent is hereby corrected as shown below:

<u>Title page,</u>
Item [30], please change the number of the priority document from "98039022" to
-- 9803922.5 --

Signed and Sealed this

Eleventh Day of December, 2001

Attest:

NICHOLAS P. GODICI
*Attesting Officer*　　*Acting Director of the United States Patent and Trademark Office*